United States Patent [19]
Collins et al.

[11] Patent Number: 5,849,267
[45] Date of Patent: *Dec. 15, 1998

[54] STABLE DESENSITIZING ANTITARTAR DENTIFRICE

[75] Inventors: Michael A. Collins, Hazlet; Richard J. Crawford, Asbury; Donald W. Clipper, Mead, all of N.J.

[73] Assignee: Colgate-Palmolive Company, New York, N.Y.

[ * ] Notice: The term of this patent shall not extend beyond the expiration date of Pat. Nos. 5,240,697, 5,503,823, 5,505,933 and 5,352,439.

[21] Appl. No.: 859,506

[22] Filed: May 20, 1997

[51] Int. Cl.$^6$ ................. A61K 7/16; A61K 7/18
[52] U.S. Cl. ................. 424/49; 424/52; 424/57
[58] Field of Search ........................... 424/49–88

[56] References Cited

U.S. PATENT DOCUMENTS

| | | | |
|---|---|---|---|
| 4,283,385 | 8/1981 | Dhabhar et al. | 424/52 |
| 4,357,318 | 11/1982 | Shah et al. | 424/52 |
| 4,989,607 | 2/1991 | Keusch et al. | 128/640 |
| 5,080,717 | 1/1992 | Young | 106/197.1 |
| 5,143,071 | 9/1992 | Keusch et al. | 128/640 |
| 5,240,697 | 8/1993 | Norfleet et al. | 424/52 |
| 5,256,402 | 10/1993 | Prencipe et al. | 424/53 |
| 5,352,439 | 10/1994 | Norfleet et al. | 424/52 |
| 5,374,417 | 12/1994 | Norfleet et al. | 424/49 |
| 5,486,350 | 1/1996 | Norfleet et al. | 424/49 |
| 5,503,823 | 4/1996 | Norfleet et al. | 424/52 |
| 5,505,933 | 4/1996 | Norfleet et al. | 424/52 |
| 5,571,501 | 11/1996 | Toy | 424/49 |
| 5,616,621 | 4/1997 | Popli et al. | 514/772.4 |

*Primary Examiner*—Shep K. Rose
*Attorney, Agent, or Firm*—Henry S. Goldfine

[57] ABSTRACT

A desensitizing anti-tartar dentifrice of low stringiness upon extrusion from a tube or other container onto a toothbrush is provided which also retains desirable cream or gel consistency without becoming thick and difficult to extrude and retains phase integrity without substantial separation, which contains polyphosphate or phosphono compound anti-tartar agent and potassium salt tooth pain inhibitor and in which the gelling agent is a mixture of alkali metal carboxymethyl cellulose, (CMC) and xanthan, wherein the CMC contains about 1.0 to 1.5 carboxymethyl groups per anhydroglycose unit.

15 Claims, No Drawings

STABLE DESENSITIZING ANTITARTAR DENTIFRICE

BACKGROUND OF THE INVENTION

This invention relates to a stable desensitizing anti-tartar dentifrice.

Dentifrices have long been used to clean and polish teeth. Increasingly, over the years, active ingredients have been included in dentifrice preparations to provide additional prophylactic or oral health advantages; for instance anticaries agents such as fluorides; antiplaque agents such as cationic or non-cationic antibacterial agents, anti-tartar agents such as polyphosphates, dentine sensitivity reducing agents such as potassium salts and the like.

When an active agent is added to dentifrice compositions, singly or in combination, it is important to consider its compatibility with other ingredients of the dentifrice.

For instance, an effective desensitizing anti-tartar dentifrice is described in U.S. Pat. No. 5,240,697, the disclosure of which is incorporated herein by reference. This dentifrice contains an anti-tartar agent such as polyphosphate or a phosphono compound and a dentine desensitizing agent, such as a potassium salt.

It has been observed that when such a desensitizing anti-tartar dentifrice is prepared its long term effectiveness is limited by the tendency of liquids and solids in the dentifrice to undergo syneresis and separate into phases upon aging when sodium carboxymethyl cellulose having about 0.7 carboxymethyl groups per anhydroglucose unit in its molecule is employed as a dental cream or toothpaste gelling agent. Grades of such sodium carboxymethyl cellulose presently are generally available in commerce and frequently used in dentifrices, with the number "7" affixed to the product; for instance, CMC-7MF and CMC-7MXG, each available from Hercules, Inc. In this regard it is noted that a commercial dentifrice designed to desensitize sensitive teeth containing, i.e., potassium nitrate, sodium bicarbonate, trisodium pyrophosphate, xanthan and cellulose gum, by infrared analysis that the cellulose gum has the characteristics of CMC-7MF.

This separation tendency has been reduced by employing the "12" grade of sodium carboxymethyl cellulose as gelling agent in sensitizing anti-tartar dentifrice, for instance CMC-12M31P, also available from Hercules. In the CMC-12 grades, there are about 1.2 carboxymethyl groups per anhydroglucose unit in the molecule. Indeed, CMC-12M31P is employed in Example 2 of U.S. Pat. No. 5,240,697. However, even with a CMC 12 grade, product stringiness, progressive dentifrice thickening and separation over time can be observed. U.S. Pat. No. 5,240,697 also contains a statement that it is preferred that the gelling agent be "carrageenan carboxymethylcellulose or xanthan or a mixture of about equal parts of each". However, a mixture of xanthan and CMC 12 grade is not disclosed.

It is an advantage of this invention that a stable desensitizing anti-tartar dentifrice is provided.

It is a further advantage of this invention that a desensitizing anti-tartar dentifrice having low stringiness upon extrusion from a tube or other container onto a toothbrush is provided which also retains desirable cream or gel consistency without becoming thick and difficult to extrude and likewise retains phase integrity without substantial separation.

Other advantages of the invention will be apparent from consideration of the following description.

In accordance with certain of its aspects, this invention relates to a stable desensitizing anti-tartar dentifrice comprising (a) a dentifrice vehicle of liquids comprising water and humectant and solids comprising about 0.1–4% by weight of a mixture of gelling agent to provide said dentifrice with a creamy or gel consistency, (b) an effective anti-tartar proportion of an alkali metal polyphosphate or a phosphono antitartar agent and (c) a desensitizing proportion of a tooth pain inhibiting potassium salt, wherein said gelling agent is alkali metal carboxymethyl cellulose (CMC) containing about 1.0 to 1.5 carboxymethyl (CM) groups per anhydroglucose (AG) unit therein and xanthan (X) and the weight ratio of said CMC to said X being from about 3:1 to about 1:3.

The mixed gelling agent as the solid portion of the dentifrice vehicle employed in the present invention is present in the dentifrice in amount of about 0.1–4% by weight, preferably about 0.5–2% and most preferably about 0.8–1.2% to provide the dentifrice with a creamy or gel consistency. The mixed gelling agent-thickening agent contains an alkali metal CMC gelling agent in which there are present about 1.0–1.5 CM groups, e.g., 1.0, 1.1, 1.2, 1.3, 1.4 or 1.5 CM groups, preferably about 1.2 units, per AG unit and is present with the xanthan in weight ratio of CMC:X of about 3:1 to about 1:3, preferably about 3:1 to about 1:1 and most preferably about 2:1.

The preferred alkali metal CMC is CMC 12M31P, available from Hercules, Inc.

Xanthan is commercially available from Kelco.

When incorporating the gelling agent components into a dentifrice they are typically added to an aqueous humectant liquid or as a premixture of the CMC and the LC.

In addition to the CMC—X mixture, if desired, up to about 15%, preferably about 5–10%, by weight of the amount of gelling agent plus thickening agent can be comprised of other gelling or thickening ingredients such as a hydroxyethyl cellulose, hydroxyethylpropyl cellulose, hydroxyethyl methyl cellulose, hydroxypropylmethyl cellulose, gum tragacanth, polyvinyl pyrrolione, synthetic hectorite such as Laponite® or even kappa carrageenan (Irish moss) or the "7" grade of alkali metal carboxymethyl cellulose, e.g., CMC7MF, CMC7MFX. Further, if desired up to about 15%, preferably about 5–10% of the thickening agent can be comprised of other non-gelling thickeners such as commercially available inorganic thickening grades of silica such as Syloid® 244 and synthetic hectorite, such as Laponite®. A particularly desirable non-gelling thickener is lambda carrageenan, which is described in mixture with CMC-12 grades in applicants' copending application, U.S. Ser. No. 08/756,095, filed Nov. 22, 1996, the disclosure of which is incorporated herein by reference.

The orally acceptable vehicle or base for the invented dentifrices will normally include water, humectant, surfactant or detergent, and polishing agent. The water employed may be any potable water but it is preferred that it should be of less than 200 p.p.m. of hardness as $CaCO_3$, and more preferably less than 100 p.p.m. of hardness. Most preferably deionized and irradiated water will be employed. The liquid vehicle comprising water and humectant comprises about 20–80% by weight of the dentifrice. The humectant component of the dentifrice may comprise a mixture of several humectants, such as glycerol, sorbitol and polyethylene glycol, but other mixtures of humectants and single humectants may also be employed. Among other humectants that are useful are propylene glycol and polypropylene glycols. A normal range of molecular weights for the polyethylene glycol humectants is 200 to 1,000, preferably 400 to 600 or 800, e.g., about 600. The water content of the dentifrice may be about 3–50% by weight and the humectant content about 10–80% by weight. In visually clear gel (transparent or translucent) toothpastes in which the refractive index is an important consideration, the liquid portion of the dentifrice may be about 3–30% by weight of water and 10% to 80% by weight of glycerine or sorbitol (70% aqueous solvent) or mixture thereof The polyphosphates that are components of the invented compositions may be any of various water soluble polyphosphates, including alkali metal pyrophosphates, such as tetrapotassium pyrophosphate, trisodium pyrophospate, dipotassium pyrophosphate, tetrasodium pyrophosphate and disodium pyrophosphate, with the sodium salts being preferred. Instead of the pyrophosphates, the tripolyphosphates and other polyphosphates, such as the hexametaphosphates, may be substituted, at least in part. The pyrophosphates are considered to be superior as anti-tartar agents that help to desensitize the teeth. A most preferred pyrophosphate is tetrasodium pyrophosphate, but the corresponding tetrapotassium pyrophosphate or tri, -di and mono sodium and potassium pyrophosphates may also be used, at least in part. The polyphosphates act in these claimed composition to inhibit tartar development on the teeth that are brushed or otherwise treated with the invented compositions. In conjunction with the desensitizing agents mentioned, they improve the desensitizing effects thereof and help to make brushing or other treatment of the teeth painless, while at the same time counteracting the development of tartar on the teeth surfaces and near the gums, which can lead to gum irritation and disease.

Another desirable component of the present compositions, particularly when pyrophosphate salt is employed, is a synthetic anionic polymeric polycarboxylate (SAPP), which acts as a stabilizer for the polyphosphate anti-tartar agent and apparently helps to block access of painful or pain-causing materials, such as sugars, to the tooth nerves. The SAPP's employed in the invented compositions include free acidic forms thereof, as well a water soluble salts of such acids, and very preferably such compounds will be in salt form and the salt will be a sodium or potassium salt, which acts to improve desensitizing effects of the oral compositions of the invention. Such salts may be starting materials or the acidic forms may be partially or fully neutralized, as by NaOH or KOH, during the process of manufacturing the toothpaste. Full neutralization is highly preferred, and is often effected during the making of the toothpaste. The SAPP when present, typically comprises on a solids basis, up to about 4% by weight of the dentifrice, preferably about 0.5–3%, independent of the gelling agent/ thickening agent solid portion of the dentifrice vehicle.

The SAPP-type products are preferably polycarboxylates, typically of M.W.'s in the 5,000 to 2,000,000 range, preferably 30,000 or 50,000 to 1,100,000 or 1,500,000 and more preferably about 50,000 to 1,100,000 and most preferably 50,000 to 100,000, as determined by vapor pressure osmometry. Such SAPP's are preferably 1:4 to 4:1 copolymers of maleic anhydride and/or maleic acid with another polymerizable ethlenically unsaturated monomer, which is very preferably methyl vinyl ether. By a different method for measuring molecular weights of polymers, gel permeation chromatography against a polyethylene glycol standard, the molecular weights of preferred SAPP's may be found to be in the range of 500,000 to 1,500,000 and more preferably 1,000,000 to 1,100,000, e.g., about 1,090,000. Useful such SAPP's include Gantrez® S-97, AN-119, AN-139 and AN-169, all manufactured by GAF Corporation, which have been reported by the manufacturer to have molecular weights of 70,000, 250,00, 500,000 and 750,000, respectively. Equivalent SAPP's to the Gantrezes are sold by BASF, A.G. in Europe under the Luviform® trademark. However by gel permeation chromatography Gantrez S-97 is determined to be of a molecular weight in the range of 1,000,000 to 1,100,000. The lower molecular weight that had been determined, 70,000, had been measured by vapor pressure osmometry. The mentioned Gantrezes are all linear copolymers but crosslinked polymers, such as Carbopols® 934, 940 and 941 may be substituted for them, at least in part (1% or more). Descriptions of such polymeric materials and of other dentifrice components are contained in U.S. Pat. Nos. 4,627,977, and 5,096,699 and British Patent Specification 2235133, the disclosures of which are incorporated herein by reference, as are disclosures of all other patents, applications and publications mentioned in this specification.

Instead of the mentioned polymeric polycarboxylates other SAPP types can be substituted, preferably only in part, by polysulfonates, polysulfonates and polyphosphonates, typically up to half the SAPP content. The various polymers of such types may be made by reacting an ethylenically unsaturated organic acid, such as maleic, crotonic, sorbic, alphachlorosorbic, cinnamic, muconic, itaconic, citrconic, mesaconic, glutaconic, aconitic, angelic, umbellic or fumaric, acid(s) or anhydride(s), with an appropriate polymerized ethylenically unsaturated carboxylic, sulfonic sulfuric or phosphonic acid that contains an activated carbon-to-carbon olefinic double bond and at least one carboxylic, sulfonic, sulfuric or phosphonic group. Other olefinic monomers that are copolymerizable with the described acids or anhydrides include vinyl acetate, vinyl chloride, dimethyl maleate, and similar unsaturated monomers, and the copolymers made will contain a sufficient proportion of acidic groups or neutralized or neutralizable acidic groups to make them water soluble or swellable. Some such polycarboxylate copolymers are those disclosed in U.S. Pat. Nos. 4,138,477 and 4,183,914, and include copolymers of maleic anhydride with styrene, isobutylene or vinyl ethyl ether, polyacrylic, polyitaconic and polymaleic acids, and sulfoacrylic oligomers of comparatively low molecular weights, such as Uniroyal® ND-2.

Although Gantrez is preferred, also useful in the present compositions as SAPP's or as substitutes for them in part are carboxyvinyl polymers, such as those described in U.S. Pat. Nos. 3,711,604, 3,911,104, 3,919,409, 3,935,306 and 3,980, 767, wherein they were employed as components of toothpastes. Such materials are the Carbopols, mentioned previously, which are polymers of polyacrylic acid crosslinked with minor proportions of polyallyl sucrose or polyallyl pentaerythritol, as crosslinking agents. Instead of such polymers there may be employed polycarbophil, which is polyacrylic acid crosslinked with divinyl glycol.

In place of the polyphosphates, the anti-tartar agent may be a phosphono compound such as azacyloalkane-2,2-diphosphosphonic acid, preferably azacycloheptane-2,2-diphosphonic acid, phosphonopropane tricarboxylic acid, phosphono butane-1,2,4-tricarboxylic acid and ethanedihydroxy diphosphonic acid and water soluble salts thereof.

The anti-tartar agent is employed in an effective anti-tartar amount which is generally about 0.1 to 10% by weight of the dentifrice, preferably about 0.8 to 7%, e.g. about 2% of tetrasodium pyrophosphate or about 0.85% of azacycloheptane-2,2-diphosphonic acid, sodium salt.

The desensitizing tooth pain inhibiting potassium salts utilizable in this invention include potassium nitrate, potassium citrate and potassium oxalate, with the first two being preferred. Mixtures including at least one of such salts are also useful, and in some circumstances they may also be mixed with other water soluble potassium salt(s), which are also capable of releasing potassium ions into the toothpaste and into the mouth and onto the teeth. However, care should be taken in choosing such other potassium salts to ensure that they do not cause the composition to taste objectionably salty or have other undesirable flavor. It has been found that potassium nitrate and potassium citrate, in the proportions employed in the invented compositions, do not taste objectionably salty or otherwise interfere with the desired taste of the composition, especially when a mint/menthol flavor is employed therein. The desensitizing potassium salt is employed in a desensitizing proportion which is generally about 2 to 10% by weight of the dentifrice, preferably about 3–7%.

The composition may desirably contain a water soluble fluoride or source of fluoride ions. When the anti-tartar agent is a polyphosphate, and particularly a pyrophosphate, the water soluble fluoride or source of fluoride ions for the present compositions also helps to stabilize the pyrophosphate against enzymatic attack while also contributing its tooth hardening and anti-caries properties to the compositions. It may be slightly soluble in water, highly soluble or fully soluble, so long as it can provide such ions for use in the mouth. The source of fluoride ions is usually inorganic and a salt and is characterized by an ability to release fluoride ions in water and by relative inertness toward other components of the oral compositions. Among the useful sources of fluoride ions are water soluble alkali metal fluorides, such as sodium and potassium fluorides, cuprous fluoride, tin fluorides, such as stannous fluoride, ammonium fluorosilicate, sodium and ammonium fluorozirconates, sodium and potassium monofluorophosphates, aluminum fluorophosphates (mono-, di- and tri), and fluorinated sodium calcium pyrophosphate. When a water soluble fluoride or fluoride source is present, the proportion thereof will usually be that which provides about 100 to 2,300 p.p.m. of fluoride ion ($F^-$) and preferably about 400 to 1,500 p.p.m. of $F^-$ in the composition. For instance, 0.243% of NaF provides about 1,000 p.p.m. of $F^-$.

The polishing agents for the dentifrice bases may be water soluble, such as sodium bicarbonate, or more frequently water insoluble materials which are sometimes referred to as abrasives, but which term is not intended to indicate removal of tooth material but rather to removal of deposits on dental enamel from and polishing the teeth. Preferred polishing agents are siliceous materials, such as silica, and will normally be of fine particles, such as those of a mean particle size up to about 10 microns and of a very high surface:volume ratio, which may be as much as 250 square meters/gram. A preferred silica is a precipitated amorphous hydrated silica, such as Zeodent® 113 or 115, marketed by J. M. Huber Corporation, but other polishing agents may be employed too, including water-insoluble sodium metaphosphate, potassium metaphosphate, tricalcium phosphate, calcium phosphate dihydrate, anhydrous dicalcium phosphate, calcium pyrophosphate magnesium orthophosphate, trimagnesium phosphate, calcium carbonate, alumina trihydrate, aluminum silicate, zirconium silicate, calcined alumina, bentonite, silica gel or colloidal silica, and complex amorhous alkali metal aluminosilicates and mixtures thereof. Still other suitable polishing materials include the particulate thermosetting resins described in U.S. Pat. No. 4,070,510, such as melamine-, phenolic-, and urea-formaldehydes, and crosslinked polyepoxides and polyesters.

When visually clear gels are desired, a polishing agent of colloidal silica, such as those which have been sold under the trademark SYLOID® as Syloid 72 and Syloid 74 or under the trademark Santocel® as Santocel 100, and alkali metal aluminosilicate complexes thereof are particularly useful, since they have refractive indices close to the refractive indices of gelling agent-liquid (including water and/or humectant) systems that are often used in dentifrices. The polishing agent in the dentifrice generally comprises about 10–50% weight thereof The surface active agents or surfactant is generally employed and will normally be a water soluble detergent, which is useful to clean the teeth (and gums) and helps the anti-tartar and desensitizing components of the composition to contact the tooth surfaces and to penetrate into the dentin and pulp, where exposed. Such detergents have useful foaming properties and also aid in producing a uniform toothpaste, in which the active components are evenly distributed, so that each toothbrush full of toothpaste will contain effective proportions of such materials. The organic surface-active material is preferably anionic, nonionic or ampholytic in nature, and most preferably is anionic. Suitable examples of anionic surfactants are higher alkyl sulfates such as sodium or potassium lauryl sulfate, higher fatty acid monoglyceride monosulfates, such as the potassium salt of the monosulfated monoglyceride of hydrogenated coconut oil fatty acids, alkyl aryl sulfonates such as potassium dodecyl benzene sulfonate, higher fatty sulfoacetates, higher fatty acid esters of 1,3-dihydroxy propate sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium of potassium salts of N-lauroyl, N-myristoyl, or N-palmitoyl sarcosine which should be substantially free from soap or similar higher fatty acid material.

Examples of water soluble nonionic surfactants are condensation products of ethylene oxide with various hydrogen-containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials). Of the mentioned detergents the higher fatty alcohol sulfates are preferred (in such detergents and in the other detergents mentioned, and elsewhere in this specification "higher", when employed in designating alkyl groups, fatty acids, etc., identifies such as containing 10 to 20 carbon atoms, preferably 12 to 18, which preferably are in linear arrangement). Surfactants are generally employed in the amount of about 0.05 to 10% by weight, preferably about 0.5–5%.

Various other components or toothpastes may be considered to be additional active materials or adjuvants. Included in this group are: other anti-tartar or anti-calculus compounds, such as zinc compounds, such as zinc chloride, zinc acetate and zinc oxide, antibacterial antiplaque agents, such as sanguinaria extract or triclosan; buffers to control pH; bleaching agents and tooth whiteners, such as percompounds; preservatives; sweeteners, such as potassium (or sodium) saccharin or cyclamate, acesulfam-K, sucralose and aspartame; flavors, such as mint (peppermint and spearmint) and methol; and dyes and pigments, such as chlorophyll and titanium dioxide. Pigment will be titanium dioxide (rutile), and the proportion thereof will normally be in the range of 0.2% to 1%, preferably 0.4 to 0.8% and more preferably 0.4 to 0.6%, e.g., about 0.5%. The sweetener content will normally be that of an artificial or synthetic sweetener (non-sugar) and the normal proportion thereof present will be in the range of 0.2 to 0.8%, preferably 0.3 to 0.7% and more preferably 0.4 to 0.6%, e.g., about 0.5%, although for cyclamate salt sweeteners such range is typically 3 to 5%. The flavor content, which is preferably of a mixed peppermint/menthol flavor, will usually be in the range of 0.5 to 2%, preferably 0.7 t 1.5% and more preferably 0.8 to 1.2%, e.g., about 1%. F.D. & C. Grade dyes may be used in appropriate amounts to provide desired colors. The contents of other components or adjuvants of the toothpaste formula will normally not exceed 10%, often will be less than 5%, and they can be absent.

To make the dentifrices a particular process is preferred because it results in excellent toothpastes which are of the desired pH and viscosity, and in which the active components are of improved stabilities. In such process glycerin and polyethylene glycol (for instance, polyethylene glycol 600) components of the humectant are mixed together first in a conventional mixer and then with a pre-mix of the gelling agent, followed by dispensing copolymer (if present) and anti-tartar agent in the mixture, with mixing continued until the mixture becomes a slurry which is smooth in appearance, after which sorbitol is admixed with the smooth slurry and water is added and the desensitizing agent(s) is/are admixed with the thinned slurry. When the copolymer is present it may be introduced into the mixture before, together with or after the antitartar agent. All such mixings are at room temperature, in the range of about 20° to 30° C. Next, the gel phase produced may be heated to a temperature in the range of about 55° to 75° C., with mixing, and mixing continued for about 10 to 30 minutes after such elevated temperature has been reached. The copolymer, if present and if initially in acidic form, is then neutralized with alkali metal hydroxide, preferably potassium hydroxide, to a pH in the range of about 6 to 8, preferably about 7, with mixing, and such mixing is continued for another about 10 to 30 minutes after completion of the addition of the alkali metal hydroxide. Then the resulting gel phase, if heated, is cooled to a temperature in the range of about 35° to 45° C., after which the siliceous polishing agent is admixed with the gel phase and mixing is continued for an additional 10 to 30 minutes under a vacuum in the range of about 5 to 100 millimeters of mercury, preferably about 5 to 50 mm. Hg, resulting in production of a paste or gel. The last step of the process (excluding additions of pigment, flavor, sweetener and other adjuvants) is the admixing of surfactant, preferably anionic detergent, with the dentifrice paste or gel, which is followed by mixing for another 3 to 10 minutes under a vacuum of 5 to 50 mm. Hg. The product resulting is a stable anti-tartar desensitizing toothpaste which is of a viscosity like that of normal toothpastes, about 100,000 to 500,000 centipoises, of a pH in the range of about 6 to 8, preferably about 6.5 to 7.5, e.g., about 7, of satisfactory flavor, (especially when a mint/menthol flavor is present), and not excessively salty. In the above description of the manufacturing method a humectant mixture is employed and no flavor, sweetener and pigment additions are mentioned. If the humectant mixture or of any other optional component (s) of the formula is/are not present in the formula the additional steps mentioned above that apply to such components may be omitted. Also, the sweetener and pigment may be added with the thickener, copolymer, fluoride and polyphosphate to the glycerol/polyethylene glycol mixture and the flavor may be added with the surfactant near the end of the procedure.

The dentifrices may be made by other methods than that described above but it has been found that the described procedure results is preferred. Gel dentifrices may be made in substantially the same manner, with normal adjustments of the formula components and proportions known to those of skill in the toothpaste formulation art.

In the preferred practice of this invention the composition according to this invention such as a dentifrice is preferably applied regularly to dental enamel, such as every second or third day or preferably from 1 to 3 times daily, at a pH of about 4.5 to about 9, generally about 5.5 to about 8, preferably about 6 to 8, for at least 2 weeks up to 8 weeks or more up to lifetime.

The following examples are further illustrative of the nature of the present invention, but it is understood that the invention is not limited thereto. All amounts and proportions referred to herein and in the appended claims are by weight.

EXAMPLE 1

The following anti-tartar sensitivity reducing dentifrice is prepared by the preferred process described above with Gantrez copolymer introduced after tetrasodium pyrophosphate:

| Ingredient | Parts by Weight |
| --- | --- |
| Water | 27.907 |
| Glycerin | 10.000 |
| Sorbitol (70%) | 22.700 |
| Xanthan | 0.300 |
| Sodium CMC 12M31P | 0.300 |
| Sodium Fluoride | 0.243 |
| Sodium Saccharin | 0.350 |
| Potassium Hydroxide (50%) | 1.400 |
| Gantrez S-97 (pwdr) | 1.500 |
| Tetrasodium Pyrophosphate | 2.000 |
| Polyethylene Glycol 600 | 3.000 |
| FD&C Blue #1 (1% sol) | 0.300 |
| Potassium Nitrate | 5.000 |
| Silicon Dioxide Zeodent 115 | 23.000 |
| Flavor | 0.800 |
| Sodium Lauryl Sulfate | 1.200 |

The dentifrice is incorporated into a laminated plastic toothpaste tube. Upon extrusion onto a toothbrush, it is a neat non-stringy ribbon. Upon aging at each of (a) ambient conditions in the tube for 24 months and (b) at 49° C. for 12 weeks, it remains stable without syneresis. When sodium CMC-12M31P is replaced by sodium CMC-7MFN, syneresis is observed with the liquid and solid phases separating upon aging at 49° C. for four weeks and at room temperature for 12 weeks.

Potassium hydroxide is a desirable neutralizing agent for this dentifrice in which the Gantrez® polycarboxylate is present since the polycarboxylate absorbs potassium ion from the neutralizing agent, thereby keeping active potassium ion available from the potassium nitrate to effect reduction in tooth sensitivity when the dentifrice is applied regularly to the teeth.

EXAMPLE 2

The following anti-tartar, sensitivity reducing dentifrice is prepared by the preferred process described above with Gantrez copolymer introduced together with sodium tripolyphosphate:

| Ingredient | Parts by Weight |
| --- | --- |
| Water | 26.907 |
| Glycerin | 10.000 |
| Sorbitol (70%) | 22.700 |
| Xanthan | 0.300 |
| Sodium CMC 12M31P | 0.300 |
| Sodium Fluoride | 0.243 |
| Sodium Saccharin | 0.350 |
| Potassium Hydroxide (50%) | 1.400 |
| Gantrez S-97 (pwdr) | 1.500 |
| Sodium Tripolyphosphate | 3.000 |
| Polyethylene Glycol 600 | 3.000 |
| FD&C Blue #1 (1% sol) | 0.300 |
| Potassium Nitrate | 5.000 |
| Silicon Dioxide Zeodent 115 | 23.000 |
| Flavor | 0.800 |
| Sodium Lauryl Sulfate | 1.200 |

EXAMPLE 3

The following anti-tartar, sensitivity reducing dentifrice is prepared by the preferred process described above with Gantrez copolymer introduced before azacyceloheptane-2, 2-diphosphonic acid, sodium salt:

| Ingredient | Parts by Weight |
| --- | --- |
| Water | 29.052 |
| Glycerin | 10.000 |
| Sorbitol (70%) | 22.700 |
| Xanthan | 0.300 |
| Sodium CMC 12M31P | 0.300 |
| Sodium Fluoride | 0.243 |
| Sodium Saccharin | 0.350 |
| Potassium Hydroxide (50%) | 1.400 |
| Gantrez S-97 (pwdr) | 1.500 |
| Azacycloheptane-2-,2-diphosphonic Acid, sodium salt | 0.855 |
| Polyethylene Glycol 600 | 3.000 |
| FD&C Blue #1 (1% sol) | 0.300 |
| Potassium Nitrate | 5.000 |
| Silicon Dioxide Zeodent 115 | 23.000 |
| Flavor | 0.800 |
| Sodium Lauryl Sulfate | 1.200 |

The invention has been described in conjunction with illustrative embodiments thereof but is not to be considered to be limited to these because one of skill in the art will be able to utilize substitutes and equivalents thereof without departing from the bounds of the invention and the spirit thereof.

We claim:

1. A stable desensitizing anti-tartar dentifrice consisting essentially of a dentifrice comprising (a) a dentifrice vehicle of liquids comprising water and humectant and solids comprising about 0.1–4% by weight of a mixture of gelling agent to provide said dentifrice with a creamy or gel consistency, (b) an effective anti-tartar proportion of an alkali metal polyphosphate or a phosphono antitartar agent and (c) a desensitizing proportion of a tooth pain inhibiting potassium salt, wherein said gelling agent is alkali metal carboxymethyl cellulose (CMC) containing about 1.0 to 1.5 carboxymethyl (CM) groups per anhydroglucose (AG) unit therein and Xanthan (X) and the weight ratio of said CMC to said X being from about 3:1 to about 1:3.

2. The stable desensitizing anti-tartar dentifrice claimed in claim 1 wherein said solids of said dentifrice vehicle are present in amount of about 0.5–2% by weight.

3. The stable desensitizing anti-tartar dentifrice claimed in claim 2 wherein said solids are present in amount of about 0.8–1.2%.

4. The stable desensitizing anti-tartar dentifrice claimed in claim 2 wherein the weight ratio of (a) to (b) is about 3:1 to about 1:1.

5. The stable desensitizing anti-tartar dentifrice claimed in claim 4 wherein the weight ratio of alkali metal (a) to (b) is about 2:1.

6. The stable desensitizing anti-tartar dentifrice claimed in claim 2 wherein said alkali metal CMC contains about 1.2 carboxymethyl groups per anhydroglucose group.

7. The stable desensitizing anti-tartar dentifrice claimed in claim 1 wherein an alkali metal pyrophosphate is present in an effective anti-tartar proportion of about 0.1–1.0%.

8. The stable desensitizing anti-tartar dentifrice claimed in claim 7 wherein said alkali metal pyrophosphate is a sodium pyrophosphate and is present in amount of about 2–7% by weight.

9. The stable desensitizing anti-tartar dentifrice claimed in claim 8 is wherein said sodium pyrophosphate is tetrasodium pyrophosphate, present in amount of about 2% by weight.

10. The stable desensitizing anti-tartar dentifrice claimed in claim 1 wherein said potassium salt is selected from the group consisting of potassium nitrate, potassium citrate and potassium oxalate and is present in amount of about 1–10% by weight.

11. The stable desensitizing anti-tartar dentifrice claimed in claim 10 wherein said potassium salt is potassium nitrate and is present in amount of abut 3–7% by weight.

12. The stable desensitizing anti-tartar dentifrice claimed in claim 10 wherein said dentifrice contains a synthetic anionic polymeric polycarboxylate in amount of up to about 4% by weight.

13. The stable desensitizing anti-tartar dentifrice claimed in claim 7 wherein said dentifrice contains a water soluble fluoride or source of fluoride ions in amount to provide about 100 to 2,300 p.p.m. of fluoride ion.

14. A process for preparing the stable desensitizing antitartar dentifrice claimed in claim 1 wherein humectants comprising glycerin and polyethylene glycol are mixed with each other and then mixed with a pre-mix of said gelling agents, followed by dispersing said antitartar agent in the mixture, continuing to mix until a smooth-appearing slurry is formed, followed by mixing therewith sorbitol humectant, water and said potassium salt, all mixing to this point being at about 20° to 30° C.; heating the thus formed gel phase to about 55° to 75° C. while mixing and continuing to mix about 10 to 30 minutes after the heated temperature is reached, cooling to about 35° to 45° C. and admixing the gel phase with a siliceous polishing agent and continuing to mix for about 10 to 30 minutes in a vacuum of about 5 to 100 mm Hg, thereby forming said dentifrice.

15. The process claimed in claim 14 wherein a synthetic anionic polymeric polycarboxylic acid is dispersed in the mixture before, together with or after said antitartar agent and after said mixing for about 10 to 30 minutes after the heated temperature or about 55° to 75° C. has been reached, neutralizing said polycarboxylic acid with potassium hydroxide to a pH of about 6 to 8, with mixing, and continuing to mix for about 10 to 30 minutes after completion of the addition of potassium hydroxide after which the gel phase is cooled to about 35°°C. to 45° C. and said polishing agent is added.

* * * * *